US00PP31173P2

(12) United States Plant Patent
Kleinwee

(10) Patent No.: US PP31,173 P2
(45) Date of Patent: Dec. 3, 2019

(54) ***PETUNIA* PLANT NAMED 'PEHY0039'**

(50) Latin Name: *Petunia hybrida*
Varietal Denomination: PEHY0039

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,670

(22) Filed: Apr. 5, 2018

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21
CPC ..... A01H 6/824; A01H 5/02
See application file for complete search history.

*Primary Examiner* — Keith O. Robinson
(74) *Attorney, Agent, or Firm* — Dale Skalla

(57) ABSTRACT

A new *Petunia* plant named 'PEHY0039' particularly distinguished by its relatively small sized, cup shaped flowers with a deep salmon colored star shaped pattern on a light salmon background, mid early flowering and a trailing plant habit.

1 Drawing Sheet

Latin name of the genus and species of the plant claimed: *Petunia hybrida.*

Varietal denomination: 'PEHY0039'.

BACKGROUND OF THE NEW PLANT

The present invention comprises a new *Petunia*, botanically known as *Petunia hybrida*, and hereinafter referred to by the variety name 'PEHY0039'.

'PEHY0039' is a product of a planned breeding program. The new cultivar has relatively small sized, cup shaped flowers with a deep salmon colored star shaped pattern on a light salmon background, mid early flowering and a trailing plant habit 'PEHY0039' originated from an X-ray treated cutting of variety 'PEHY0004' (U.S. Pat. No. 23,432) in April 2013 in a controlled breeding environment in Enkhuizen, The Netherlands.

In comparison with the parent, 'PEHY0039' is having a salmon colored star pattern, a light salmon colored background color, and 2 days earlier in flower, while 'PEHY0004' is having a rose colored star pattern, a light rose colored background and 2 days later in flower.

The first act of asexual reproduction of 'PEHY0039' was accomplished when vegetative stem tip cuttings were propagated from the initial selection in August 2013 in a controlled breeding environment in Enkhuizen, The Netherlands.

BRIEF SUMMARY OF INVENTION

Horticultural examination of plants grown from cuttings of the plant initiated in August 2013 and continuing thereafter, has demonstrated that the combination of characteristics as herein disclosed for 'PEHY0039' are firmly fixed and are retained through successive generations of asexual reproduction.

'PEHY0039' has not been observed under all possible environmental conditions. The phenotype may vary significantly with variations in environment such as temperature, light intensity, and day length.

A Plant Breeder's Right for this cultivar has not yet been applied for. 'PEHY0039' has not been made publicly available prior to the effective filing date of this application, notwithstanding any disclosure that may have been made less than one year prior to the effective filing date of this application by the inventor or another who obtained 'PEHY0039' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
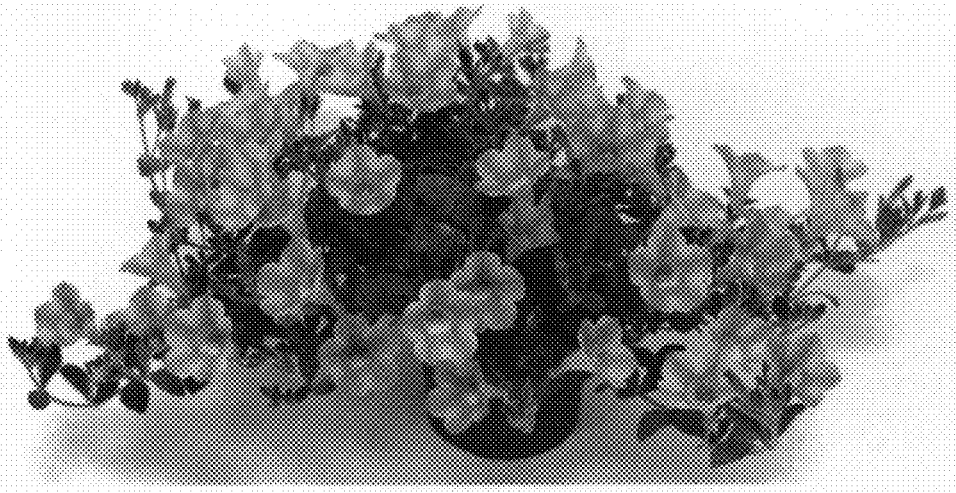
Figure 2:
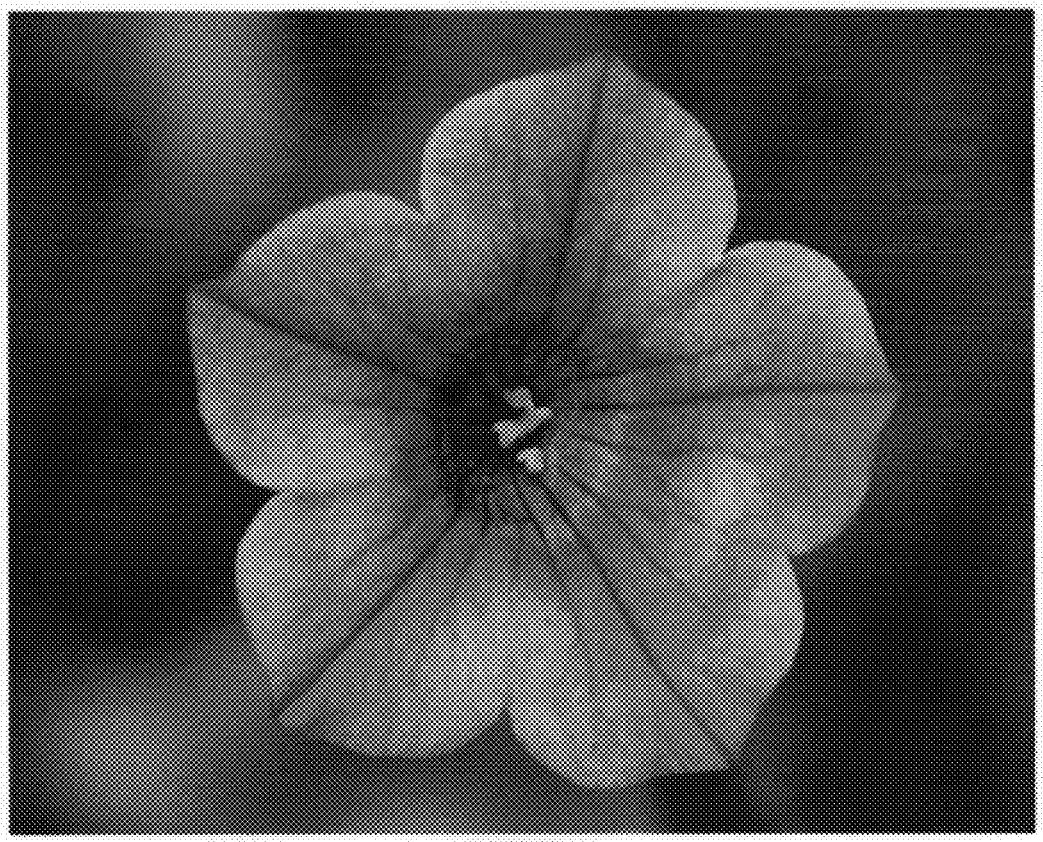

The accompanying photographic drawings show typical flower and foliage characteristics of 'PEHY0039' with colors being as true as possible with an illustration of this type. The photographic drawings show in FIG. 1. a flowering plant of the new variety and in FIG. 2. a close-up of the flowers.

DETAILED BOTANICAL DESCRIPTION

The aforementioned photographs were taken in September 2016 from plants growing outside in Andijk, The Netherlands. These plants were approximately 20 weeks of age.

The plant descriptions and measurements were taken in September 2017 in Andijk, Netherlands on 20 week old plants that were growing in baskets.

Color references are made to The Royal Horticultural Society Colour Chart (R.H.S.) 2001.

TABLE 1

DIFFERENCES BETWEEN THE NEW VARIETY 'PEHY0039' AND THE ORIGINAL VARIETY 'PEHY0004'

| | 'PEHY0039' | 'PEHY0004' (U.S. Plant Pat. No. 23,432) |
|---|---|---|
| Flower background color: | Light Salmon | Light Rose |
| Flower pattern color: | Deep salmon star pattern | Rose star pattern |
| Earliness: | Mid early | Mid early to medium, 2 days later than 'PEHY0039' |

Plant:
- *Form, growth and habit.*—Semi-trailing plant habit.
- *Plant height.*—28 cm.
- *Plant height (inflorescence included).*—32 cm.
- *Plant diameter (width).*—40-45 cm.

Roots:
- *Number of days to initiate and produce roots.*—16 days at about 22 degrees C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 144A.
- *Immature leaf, color lower surface.*—RHS 144B.
- *Mature leaf, color upper surface.*—RHS 144A.
- *Mature leaf, color lower surface.*—RHS 144B.
- *Length.*—4.2 cm.
- *Width.*—2.1 cm.
- *Shape.*—Ovate.
- *Base shape.*—Shortly Attenuate.
- *Apex shape.*—Acute.
- *Margin.*—Entire.
- *Texture, upper surface.*—Densely covered with short hair.
- *Lower surface.*—Densely covered with short hairs.
- *Color of veins, upper surface.*—RHS 144D.
- *Color of veins, lower surface.*—RHS 144D.
- *Petiole color.*—RHS 144D.
- *Length.*—0.6 cm.
- *Diameter.*—0.2 cm.
- *Petiole texture.*—Densely covered with short hairs.

Stem:
- *Quantity of main branches per plant.*—4-5.
- *Color of stem.*—RHS 144A.
- *Length of stem.*—20-25 cm.
- *Diameter.*—0.3-0.4 cm.
- *Length of internodes.*—0.1-2.5 cm.
- *Texture.*—Dense, mostly glandular short hairs.
- *Color of pedicel.*—RHS 144A.
- *Length of pedicel.*—1.5-3.0 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium early flowering in greenhouse, flowering throughout the summer months.
- *Quantity of inflorescences per plant.*—Approximately 50.
- *Lastingness of individual blooms on plant.*—About 7 days.
- *Fragrance.*—Present; spicy.

Bud (just when opening):
- *Color.*—RHS 70C, with green veins RHS 143C, RHS 54A at top.
- *Length.*—3.2 cm.
- *Width.*—0.6 cm.
- *Shape.*—Oblong.

Immature inflorescence:
- *Flower horizontal diameter.*—3.7 cm.
- *Color petals, upper surface.*—RHS 54A to RHS 54C, around veins darker than RHS 61A.
- *Color petals, lower surface.*—RHS 54D with veins RHS 143C.

Mature flower:
- *Flower horizontal diameter.*—6 cm.
- *Flower height (vertical).*—4.5 cm.
- *Color upper surface.*—RHS 54A to RHS 54C, around veins RHS 61A.
- *Color lower surface.*—RHS 55D with veins RHS 144A.
- *Apex shape.*—Rounded to slightly acuminate.
- *Margin.*—Entire.
- *Waviness of margin.*—Medium.
- *Petal lobation.*—Little.
- *Petal texture, upper surface.*—Papillose, glabrous.
- *Petal texture, lower surface.*—Some glandular hairs, more dense on veins.
- *Corolla tube color outside.*—RHS 70C with veins RHS 143C.
- *Corolla tube color inside.*—Longitudinal striped; RHS 53A and RHS 158D. At base some 157B coloration.
- *Corolla tube length.*—3.8 cm.
- *Corolla tube texture, outside.*—Rather dense and short glandular hairs.
- *Corolla tube texture, inside.*—Glabrous.

Calyx:
- *Color of sepal, upper surface.*—RHS 143A.
- *Color of sepal, lower surface.*—RHS 143B.
- *Length.*—1.2 cm.
- *Width.*—0.3 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.1 cm.
- *Style color.*—RHS 145A.
- *Style length.*—1.8 cm.
- *Stigma color.*—RHS 146C.
- *Stamens.*—
- *Quantity per flower.*—5.
- *Color of filaments.*—RHS 157C.
- *Length filaments.*—1.6 cm.
- *Anther color.*—RHS 36B.
- *Anther length.*—0.15 cm.
- *Anther shape.*—Elliptical.

*Color of pollen*.—RHS 159D.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0039' substantially as illustrated and described herein.

* * * * *